US005212299A

United States Patent [19]

Smith

[11] Patent Number: 5,212,299

[45] Date of Patent: May 18, 1993

[54] GLYCERYL AGAROSE AND BORATE COMPOSITIONS

[75] Inventor: Joshua D. Smith, Rockland, Me.

[73] Assignee: FMC Corporation, Philadelphia, Pa.

[21] Appl. No.: 698,228

[22] Filed: May 10, 1991

[51] Int. Cl.[5] .......................... C08B 37/00; C08B 37/12

[52] U.S. Cl. .......................... 536/114; 536/115; 536/120; 106/162; 106/205; 436/529

[58] Field of Search .......................... 106/162, 205; 536/3, 536/115, 114; 514/54; 530/120; 436/529

[56] References Cited

U.S. PATENT DOCUMENTS

| | | | |
|---|---|---|---|
| 3,956,273 | 5/1976 | Guiseley | 536/120 |
| 4,275,196 | 6/1981 | Shainoff | 536/116 |
| 4,312,727 | 1/1982 | Shainoff | 436/177 |
| 4,319,975 | 3/1982 | Cook | 536/52 |
| 4,374,925 | 2/1983 | Litman | 435/7.91 |
| 4,663,278 | 5/1987 | DiNello | 435/7.91 |
| 5,068,198 | 11/1991 | Gibbons et al. | 435/7.2 |
| 5,075,227 | 12/1991 | Hagen | 435/91 |

OTHER PUBLICATIONS

Shainoff, "Zonal Immobilization of Proteins and Peptides on Glyoxyl Agarose" (1987), pp. 0–40.

Scouten, "Affinity Chromatography", John Wiley & Sons, NY (1981) pp. 42–45.

Dumais & Nochumson, "Small DNA Fragment Separation and M13 Cloning Directly in Remelted NuSieve ® GTG Agarose Gels", *BioTechniques*, vol. 5, No. 1 (1987) pp. 62–64, 66 and 67.

Saiki, Gelfand, Stoffel, et al., "Primer-Directed Enzymatic Amplification of DNA With A Thermostable DNA Polymerase", *Science*, 239:487–491 (1988).

Nochumson, "Seaprep ® 15/45: A New Agarose With Low Gelling and Remelting Properties for Preparative Electrophoresis", *Electrophoresis* '81, Editors: Allen, Arnaud; Pub.: W. de Gruyter & Co. NY (1981) pp. 213–218.

Perlman, Chikarmane & Halvorson, "Improved Resolution of DNA Fragments in Polysaccharide-Supplemented Agarose Gels", *Analytical Biochemistry*, 163:247–254 (1987).

*Primary Examiner*—Ronald W. Griffin

*Attorney, Agent, or Firm*—Mark A. Greenfield; Robert L. Andersen

[57] ABSTRACT

Aqueous gel compositions and their use in electrophoresis, and anhydrous compositions useful in the preparation of the aqueous gel compositions.

The aqueous gel compositions comprise:

A. water,

B. at least one di- or tri-hydroxy $C_{2-4}$ alkyl ether moiety (preferably glyceryl) substituted agarose, and C. from about 20 to about 400 mM of at least one borate compound per liter of aqueous gel composition.

The anhydrous compositions comprise the agarose in powder form and the borate in powder or aqueous solution.

27 Claims, 3 Drawing Sheets

GLYCERYL AGAROSE AND BORATE COMPOSITIONS

BACKGROUND OF THE INVENTION

1. Field of the Invention

This invention relates to aqueous gels useful for the separation of mixtures of components, especially mixtures of biochemical components such as nucleic acids and proteins, by electrophoresis.

2. Statement of Related Art

Aqueous gels based on agarose and certain derivatives of agarose are known to the art for use in the electrophoresis of substances of biochemical origin.

Nonderivatized (native) agarose products useful in gel form for electrophoresis are commercially available, e.g. as the SeaKem® agarose line of products, a product of FMC Corporation, BioProducts Group, Rockland, Maine 04841, U.S.A.

A number of derivatized agaroses are disclosed in the prior art.

For example, U.S. Pat. Nos. 4,275,196 and 4,312,727 to Shainoff disclose gels containing glyoxal agarose for use in the electrophoretic separation of complex proteins. The glyoxal agarose is prepared by the reaction of agarose with glycidol to form glycerated agarose, which is then reacted with sodium periodate to form the glyoxal agarose. These patents, and/or the publication "Zonal Immobilization of Proteins and Peptides on Glyoxal Agarose" by J. R. Shainoff (1987) disclose using sodium orthoborate and/or cyanoborohydrides for the fixation or proteins in already formed handleable gels of glyoxal (not glyceryl) agarose.

"Affinity Chromatography", by W. H. Scouten, John Wiley & Sons, New York (pub.) (1981) discloses at section 3.1.1 that cyanogen bromide reacts with the vicinal diols of agarose to produce an "activated" agarose that subsequently can be coupled to spacer molecules containing primary amines. It is further disclosed that this method yields an (undesirable) bioselective adsorbent with anion-exchange properties.

U.S. Pat. No. 3,956,273 to Guiseley discloses alkylated, alkenylated, acylated and hydroxyalkylated agarose gels useful for electrophoresis.

U.S. Pat. No. 4,319,975 to Cook discloses a derivatized agarose gel useful for electrophoresis in which the molecular weight of the derivatizing substituent is between 100 and 1,000,000, and the substituent has a preselected conformational shape such that the pore diameter of the derivatized agarose is not reduced below 10 Angstrom units.

A number of derivatized agarose products are also currently on the market. Examples of these products are given below.

Hydroxyethylated agarose is a product of FMC Corporation, BioProducts Group, Rockland, Maine 04841 U.S.A. under the trademark SeaPlaque®.

NuSieve® GTG® agarose sieving gel is a product of FMC Corporation, BioProducts Group, Rockland, Maine 04841, U.S.A. Its use has been described in "Small DNA Fragment Separation and M13 Cloning Directly in Remelted NuSieve® GTG Agarose Gels" by Dumais & Nochumson, *BioTechnicues*, 5:62 (1987). Buffer systems disclosed in FMC Corporation literature as commonly used with NuSieve GTG agarose include: TAE (40 mM Tris, 20 mM acetate, 2 mM EDTA at pH 8.0) and TBE (89 mM Tris, 89 mM borate, 2 mM EDTA at pH 8.0). NuSieve comprises a native agarose which has first been derivatized to hydroxyethyl agarose and has then been partially depolymerized.

Another known sieving agarose is a combination of one part SeaKem® native agarose with three parts of the above described NuSieve® agarose. This combination has been disclosed as useful in Polymerase Chain Reaction (PCR) procedures by Saiki, Gelfand, Stoffel, et al., in "Primer-Directed Enzymatic Amplification of DNA with a Thermostable DNA Polymerase", *Science*. 239:486–491 (1988).

Still another known derivatized agarose sieving gel is SeaPrep® hydroxyethyl agarose, also a product of FMC Corporation, BioProducts Group, Rockland, Maine 04841 U.S.A. There is a disclosure of the use of this product for sieving electrophoresis by Nochumson, S. in *Electroohoresis* '81, 213–218, Allen & Arnaud (eds.), W. de Gruyter & Co. (pub.), New York (1981).

Also, highly derivatized agarose in degraded form is a component of the ProSieve™ gel system, a product of FMC Corporation, BioProducts Group, Rockland, Maine 04841 U.S.A. The ProSieve gel system forms discontinuous, thermo-reversible gels useful for the electrophoretic separation of proteins.

Other known sieving gel compositions include the mixture of agarose with hydroxyethyl cellulose as disclosed by Perlman, Chikarmane, and Halvorson in "Improved Resolution of DNA Fragments in Polysaccharide-Supplemented Agarose Gels", *Analytical Biochemistry*, 163:247–254 (1987).

Agarose (non-derivatized) is non-toxic, has high gel strength, low electroendosmosis and does not require free radical polymerization for gel formation. Agarose is a naturally occurring, substantially linear polysaccharide polymer which forms gels that are thermally reversible, thereby enabling separated components to be recovered from the melted gel.

Gels prepared with native (non-derivatized) agarose exhibit a characteristic coarse pore structure, a feature which renders them the preferred medium for the electrophoretic separation of large macromolecules. Generally speaking, primarily nucleic acids greater than 1000 base pairs can be resolved. Although smaller molecular weight entities can be resolved (restricted) by increasing the agarose content of the gel, this produces high viscosities in the agarose casting solutions, which make them very difficult to cast. Agarose gels are thus precluded from being used in a number of analytical and preparative procedures.

The large pore limitation of agarose gels can be diminished and their sieving action improved by forming the gels from certain agarose derivatives having a finer pore structure than the parent agarose. One preferred class of such modified agarose is hydroxyalkylated agarose produced by replacing 1 to 4 hydroxyl hydrogen atoms in the agarobiose units of the agarose polymer chain with hydroxyalkyl moieties. An especially preferred member is hydroxyethylated agarose obtained by reacting agarose with 2-chloroethanol in the presence of alkali. Gels from hydroxyethylated agarose are capable of resolving proteins of from about 50 kD to about 600 kD. Moreover, such gels have lower melting points than native agarose gels, an advantage when recovering sensitive biological substances from the remelted gels.

While derivatized agarose gels represent an advance in the art, both native agarose and the known derivatized agarose gels form casting solutions whose viscosity increases with gel concentration. This makes it difficult to prepare gels of sufficient concentration to achieve maximum sieving action.

Moreover, some of the above gels have elastic properties in need of improvement, i.e. the gels tend to break when handled because they are brittle. In addition, these prior art gels may provide inadequate separation of mixtures of proteins or relatively small DNA and RNA molecules unless the components of the mixture have relatively large differences in molecular weight.

SUMMARY OF THE INVENTION

The present invention relates to aqueous gel compositions useful in the electrophoretic resolution of mixtures of organic compounds, to anhydrous compositions useful in the preparation of the aqueous gel compositions, and to the use of the aqueous gel compositions in electrophoresis.

The inventive compositions contain as essential components at least one glyceryl agarose, and at least one borate compound present (when in a gel) in a gel-handling effective amount. Water is present where they comprise aqueous gels. It is a critical aspect of this invention that glyceryl agarose gels without the borate do not have sufficient dimensional stability to be useful in electrophoretic procedures, since such gels cannot be handled (e.g. removed from a casting mold and placed within an electrophoresis cell or chamber, or otherwise physically manipulated). The presence of at least one borate (as defined herein) in at least a gel handling effective amount, not only permits routine manipulation and handling of the gel, but also produces the very desirable electrophoresis properties of increasing sieving and resolution.

Figure 1:
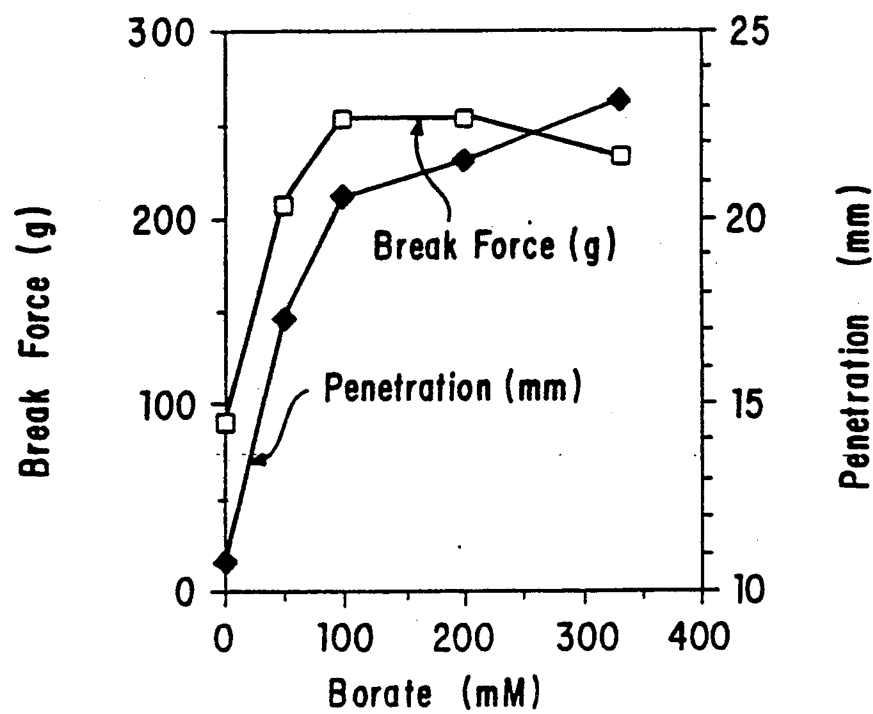
FIG. 1 shows the effects of different borate concentrations on the break force and penetration values of glyceryl agarose gels of the invention.

In the figure: NuS designates NuSieve® agarose; NuS 3:1 designates NuSieve 3:1 agarose; SPQ/B designates SeaPlaque® agarose fraction B; dNuS designates direct NuSieve agarose; GAg designates Glyceryl agarose prepared by the process of Example 2 except as note din Example 20.

DETAILED DESCRIPTION

Other than in the operating examples, or where otherwise indicated, all numbers expressing quantities of ingredients, parameters, or reaction conditions used herein are to be understood as modified in all instance by the term "about".

To avoid undue complexity, further references will be to "aqueous gel compositions," although it should be understood that this also may refer to the dry powder glyceryl agarose in combination with a dry or aqueous at least one borate compounds (either alone or as buffer ingredients) referred to previously as components (A) and (B).

Aqueous gel compositions have now been discovered that have a number of surprising and unexpected advantages over known aqueous gels used in the electrophoretic separation of mixtures of organic compounds, especially those of biochemical origin such as proteins and nucleic acids. In particular, the aqueous gel compositions of the invention:

- exhibit excellent sieving properties and can separate mixtures of biochemical compounds having relatively small differences in molecular weight;
- exhibit excellent resiliency and elasticity; superior to known agarose sieving gels;
- are crystal clear under most conditions of use;
- are effective over a wide pH range;
- exhibit a low melting point, permitting enzymatic reactions on sensitive biologicals in the presence of melted agarose gel(s);
- have exceptional stability; and
- are non-toxic.

The compositions of this invention contain the following essential components:

A. at least one glyceryl agarose present in a gel-forming effective amount;

B. at least one borate compound present in a gel-handling-effective amount; and

C. water (where it is an aqueous gel).

The glyceryl agarose plus at least one borate compositions of this invention need not only be in the form of aqueous gels. For example, this invention includes the combination of at least one glyceryl agarose powder (as defined herein) with at least one borate compound (as defined herein), in which the borate compound is a dry powder or an aqueous solution or contained as an ingredient within any electrophoretic buffer composition which buffer composition itself may be a dry powder or an aqueous solution. Thus, the inventive composition may comprise a physical mixture of (A) dry powder glyceryl agarose with (B) the at least one borate compound (in dry or aqueous form and either by itself or as a buffer ingredient). The invention also contemplates a kit for use in electrophoresis comprising separate amounts of ingredients (A) and (B) as defined above, preferably pre-measured in optimum ratios or amounts, in which the inventive glyceryl agarose and at least one borate compound aqueous gel composition is prepared by mixing components (A) and (B) with sufficient water (preferably ion-free or distilled) to form a gel composition within the concentrations disclosed herein. This invention further contemplates a method for imparting improved gel handling and sieving properties of a glyceryl agarose gel comprising admixing therewith, prior-, during-, or subsequent- to the formation of the gel, a handling-effective amount of at least one borate compound.

It should be emphasized that this invention is believed to afford a glyceryl agarose/borate gel complex, and not a simple mixture of ingredients. Thus, the gel complex preferably is formed by admixing a glyceryl agarose powder and a borate with water to form a sol and then forming the gel complex therefrom. This is best achieved by heating the glyceryl agarose powder/-borate/water mixture and then cooling the sol to below its gelling point. As an alternative, but less desirable, procedure, a glyceryl agarose aqueous gel may first be formed and the borate then introduced (as a solution) until it permeates the gel. The permeation time may vary with the manner in which permeation is effected. After or during permeation, the borate should be in contact with the glyceryl agarose for a time sufficient to make the agarose handleable.

The glyceryl agarose component (component A) of the inventive compositions is the agarose monoether of glyceryl, i.e. the 2,3-dihydroxypropyl ether of agarose. The degree of derivatization is essential to its function - too little and the resulting gel is too brittle - too much and the glyceryl agarose will not gel or will gel only poorly. It has been found that when from 0.08 to 1.3, preferably from 0.10 to 0.75, more preferably from 0.15 to 0.50, and most preferably approximately 0.27 glyceryl moieties are present per each agarobiose unit in the agarose, the glyceryl agarose provides gels having the above discussed advantages. It should be understood that the term "at least one glyceryl agarose" is used herein because all glyceryl agarose is a mixture of compounds of different polysaccharide chain lengths having different degrees of glyceryl moiety addition. All numbers used in this regard are therefore approximations based upon conventional measurements and usage.

The base agarose used to form the glyceryl agarose of the invention can be obtained from any source.

Preferred are agaroses of controlled gel strength. For uses requiring up to 3% glyceryl agarose, an agarose having a gel strength of 1000 g/cm$^2$ at 1% gel or more is particularly preferred. For uses requiring a higher final glyceryl agarose concentration a gel strength of about 1000 gm/cm$^2$ at 4% gel is particularly preferred.

Base agarose derived from Rhodophyta Gelidium or Rhodophyta Pterocladia are particularly useful, although other commercially available agaroses may be used. The best source of base agarose for preparing glyceryl agarose used herein was found to be SeaKem® LE agarose, a product of FMC Corporation, Marine Colloids Division, Rockland, Maine, U.S.A..

The glyceryl agarose can be made from agarose by the method disclosed in Example 1 of U.S. Pat. No. 4,275,196 to Shainoff, i.e. by the reaction of agarose with glycidol. However, the quantity of glycidol used in the Shainoff patent produces glyceryl agarose much too highly derivatized to be useful in the present invention. Accordingly, much smaller quantities of glycidol are employed in the preparation of the present glyceryl agarose, the specific quantity being dependent on the degree of derivatization selected within the ranges above given. Except for the use of small quantities of glycidol, the reaction is carried out as taught by Shainoff, which patent is incorporated by reference for its disclosure of this method.

The glyceryl agarose is preferably present in the aqueous gel compositions of the invention in from 0.1 to 15%, more preferably 0.5 to 8%, and most preferably from 1 to 6%, the percentages being expressed on a weight/volume basis. Glyceryl agarose is a required gelling agent present in the compositions. However, it is possible for otherwise substituted agaroses, such as hydroxyethyl agarose, to be present in varying amounts, in admixture with the inventive glyceryl agarose/borate composition.

In addition to glyceryl agarose, which is preferred, the agarose may be substituted with other di- or trihydroxy $C_{2-4}$ alkyl ether moieties such as dihydroxybutyl, dihydroxypropyl, and trihydroxypropyl.

The required at least one borate component (component B) of the present aqueous gel compositions includes water soluble boron compounds which afford a borate in solution and is one or more of the following:

a. $BH_3O_3$, b. an alkali metal borate or alkaline earth metal borate, e.g. sodium borate, potassium borate, and calcium borate, c. an alkali metal or alkaline earth metal organoboron compound, e.g. sodium boroformate and calcium borogluconate.

Where an alkaline earth metal borate is employed, since these borates are essentially insoluble in cold water, but soluble in dilute acids, an acid pH for the aqueous gel composition is strongly preferred. It is to be noted that the organoboron compounds must be other than strongly reducing compounds such as the borohydride salts and other than strongly oxidizing compounds such as the perborate salts.

Preferably the at least one borate compound is present in the aqueous gel compositions of the invention in a quantity in the range of 25 to 400 mM more preferably in the range of 40 to 150 mM, and most preferably in the range of 50 to 100 mM.

In addition to the above components of the aqueous gel compositions, other ingredients optionally can be present. These ingredients are all those conventionally employed in electrophoretic gels and do not comprise a part of this invention per se. For example, it is preferred to include from 0.1 to 10 mM, preferably from 1 to 3 mM of EDTA (ethylenediaminetetracetic acid). Also, a base such as an alkali metal hydroxide, preferably sodium hydroxide, or a mineral acid, e.g. hydrochloric acid, can also be added to adjust the pH of the composition. An additional component that can be present is Tris (trimethamine-2-amino-2-hydroxymethyl-1,3-propanediol) which acts as a buffer, and can be present in from 5 to 1000 mM. Other optional ingredients that do not adversely affect the properties of the gels also can be added.

The aqueous gel compositions of the invention have a pH in the range of from 3.0 to 12.0, preferably from 6.0 to 10.0, more preferably from 7.5 to 9.5, and most preferably from 8.0 to 8.5. The gels are extremely elastic and clear, and do not require additives to increase their handleability. They exhibit a rubbery elasticity which makes them substantially impervious to breaking under conditions of normal handling. They exhibit mechanical properties far superior to those of prior art gels, for example glyceryl agarose alone.

The nonaqueous components of the aqueous gel compositions of the invention can be packaged in convenient anhydrous form as a kit or sold separately as components. In particular, glyceryl agarose and the borate compound or compounds can be packaged together in anhydrous form in relative quantities sufficient to form the aqueous gel compositions of the invention when diluted with water at the time of use. Optional ingredients such as EDTA and pH adjusting components can then be added to the resulting diluted composition as desired. Alternatively, the aqueous gel compositions of the invention can be prepared in the form of a gel and stored and/or shipped for use in this form.

Preferably the aqueous gel compositions are formed by dissolving the glyceryl agarose component in an aqueous solution of at least one borate compound together with any optional additives. The dissolution is preferably carried out by heating until the glyceryl agarose is fully dispersed. The resulting warm sol is then poured into a cast, and allowed to cool until a strong, rigid gel has formed. An alternate (less desirable) method is to cast the aqueous gel composition in water or buffer system such as, 40 mM Tris, 20 mM Acetate, 1 mM EDTA and soak the gel in an excess of borate solution until it completely permeates the gel, which may be effected with or without an electrophoretic current applied, until the gel exhibits the desired elastic properties.

The gels of this invention are then ready for use in electrophoresis. In addition to superior handling electrophoretic purposes, which is a critical aspect of this invention, the gels of this invention also exhibit better resolution than many existing agarose sieving gels as determined by higher Ks values. The gels of the invention, for example, consistently separate 238 base pair (bp) fragments from 242 bp fragments of pBR 322 Msp 1 nucleic acids. Moreover, these gels have low fluorescence under UV light, and do not bind ethidium bromide. These factors are essential for the detection of small quantities of ethidium bromide stained nucleic acids. In addition, their low melting point (less than 65° C.) allows for subsequent enzymatic testing in the presence of molten agarose. The gels of the invention are particularly useful for the separation of nucleic acids, such as DNA and RNA (single or double stranded) in a molecular weight range below 660,000 Daltons (D), as indicated by using the pBR 322 Msp 1 digest. Similarly, they are useful for the separation of proteins below 660,000 D, and preferably below 200,000 D, such as lysozyme (14,300 D), bovine serum albumin (68,000 D), myosin heavy-chain (200,000 D), and crosslinked phosphorylase b hexamer (584,400 D).

In a further embodiment, this invention comprises prefabricated aqueous gels suitable for electrophoresis or other uses.

The invention will be illustrated but not limited by the following examples.

EXAMPLE 1

Method for Preparation of Glyceryl Agarose

(A) Standard Glyceryl Agarose

Disperse 30 g of SeaKem LE agarose in 575 ml of $dH_2O$. Dissolve agarose in microwave and adjust for lost water. Place in 80° C. hot water bath and add 4 ml of 4.4M $NaBH_4$, 14M NaOH and 20 ml of 12M NaOH. Bring temperature down to 30° C. and add 11.5 ml of pure glycidol at 0.8 drops/sec. Hold temperature at 80° C. for 1 hour and neutralize sol with 3M glacial acetic acid to a pH 6.4–6.8. Coagulate in 21 of 90% isopropyl alcohol, which is at 42° C. Wash coagulate twice in 60% isopropyl alcohol and dry in an oven overnight. Grind dried coagulate in a Willey mill using a 20 mesh (850 μm) screen.

(B) Further Purified Glyceryl Agarose

In an effort to improve the desired properties of glyceryl agarose, it was further purified by reprocessing following this protocol:

Add 10 grams of glyceryl agarose from (A) to 250 mls of 60% isopropyl alcohol (IPA), which has been heated to 40° C. Use an overhead stirrer to disperse the agarose and bring the volume up to 700 mls with 4° C. $H_2O$. Heat the solution to 80° C. on a hotplate and hold at this temperature until the solution clears and is homogeneous. Cool solution to 60° C. and add solution to 2½ volumes 99% IPA, which is at 35° C., with vigorous agitation. Allow coagulum to rest in IPA for 30 minutes, cool to <30° C. in $H_2O$ bath and then remove water from coagulum by pouring solution through a fine mesh screen. Squeeze dry coagulum and wash with 99% IPA (about 200 mls). Squeeze dry the coagulum again and wash it with 60% IPA. Squeeze dry once more and declump coagulum before drying. Dry in a 55° C. hot air oven overnight. Grind dry coagulum in a Willey mill with a 40 mesh (425 μm) screen.

EXAMPLE 2

Preparation of Glyceryl Agarose-borate Gel 1.5 grams of glyceryl agarose prepared by the process of Example 1B was added to a 250 ml Erlenmeyer flask containing a 150 ml aqueous solution of 100 mM Tris, 50 mM boric acid ($BH_3O_3$), titrated to a pH of 8.0 with sodium hydroxide or HCl. The resulting mixture was weighed, and heated in a microwave oven with intermittent swirling until the mixture became homogeneous. The resulting hot sol was cooled to 55°–65° C., reweighed, and lost water was replaced. The sol was then poured into a 70×50 mm crystallizing dish, covered, and incubated overnight at 4° C.

EXAMPLES 3–5

The process of Example 2 was repeated except that 100 mM, 200 mM, and 333 mM solutions of borate, 100 mM Tris were titrated to pH 8.0 were employed respectively instead of the quantity given in Example 2.

EXAMPLE 6

Testing of the Gels of Examples 2–5

The gels of Examples 2–5 and an identical comparison gel but without borate were tested on an Instron™ gel tester. The tests were carried out for break force and for penetration as follows:

The gels were incubated for 30 minutes in a 10° C. cold water bath. After they had equilibrated, they were inverted in the crystallizing dishes and the break force (grams) and penetration (mm) values were obtained by measuring the maximum value of each variable at failure; i.e. when the gel fractured. The Instro gel tester was used following the standard operating procedures with a 0.55 cm radius plunger at a speed of 160 mm/min.

The results are set forth in FIG. 1.

EXAMPLE 7

1.5 Grams of glyceryl agarose prepared by the process of Example IB was added to a 250 ml Erlenmeyer flask containing 150 ml of an aqueous solution of 100 mM of $BH_3O_3$ titrated to pH 7.0 with sodium hydroxide. The resulting mixture was weighed, and heated in a microwave oven with intermittent swirling until the mixture became homogeneous. The resulting hot sol was cooled to 55°–65° C., reweighed, and lost water was replaced. The sol was then poured into a 70×50 mm crystallizing dish, covered, and incubated overnight at 4° C.

EXAMPLES 8–12

The procedure of Example 7 was repeated except that the aqueous solution was titrated with sodium hydroxide to a pH of 7.5, 8.0, 8.55, 9.0, and 9.55 respectively.

EXAMPLES 13

Figure 2:
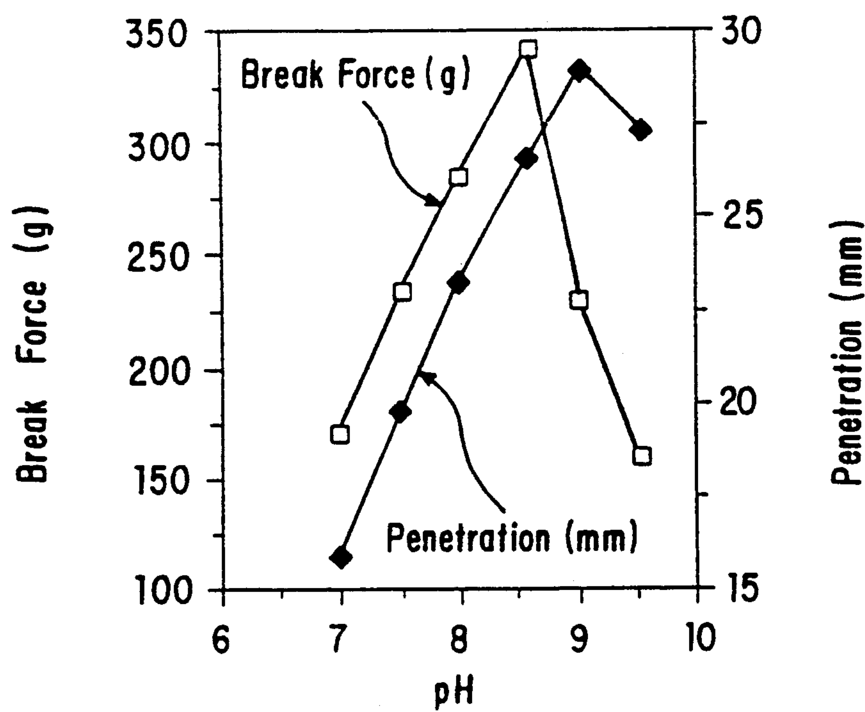
FIG. 2 shows the effects of different pH values on the break force and penetration values of glyceryl agarose gels of the invention.

The gels of Examples 7–12 were tested for break force and penetration on an Instron™ gel tester as in Example 6. The results of the tests are given in FIG. 2.

EXAMPLE 14

The break force and penetration of a glyceryl agarose gel of Example 7 of the invention was compared to that of two prior art products, NuSieve® GTG agarose and NuSieve® 3:1 (which contains 3 parts by weight of hydroxyethyl agarose and 1 part by weight of a SeaKem LE agarose). The results are given below:

Gels were made following the procedure of Example 2, with the exception that they were made up in 89 mM Tris, 89 mM borate, and 2 mM EDTA (pH of 8.0). The gels were tested on an Instron gel tester as in Example 6.

| Agarose | Break Force (g) | Penetration (mm) |
|---|---|---|
| NuSieve GTG | 60 | 4.6 |
| NuSieve 3:1 | 166 | 5.2 |
| glyceryl agarose | 190 | 21.4 |

EXAMPLES 15-18

Figure 3:
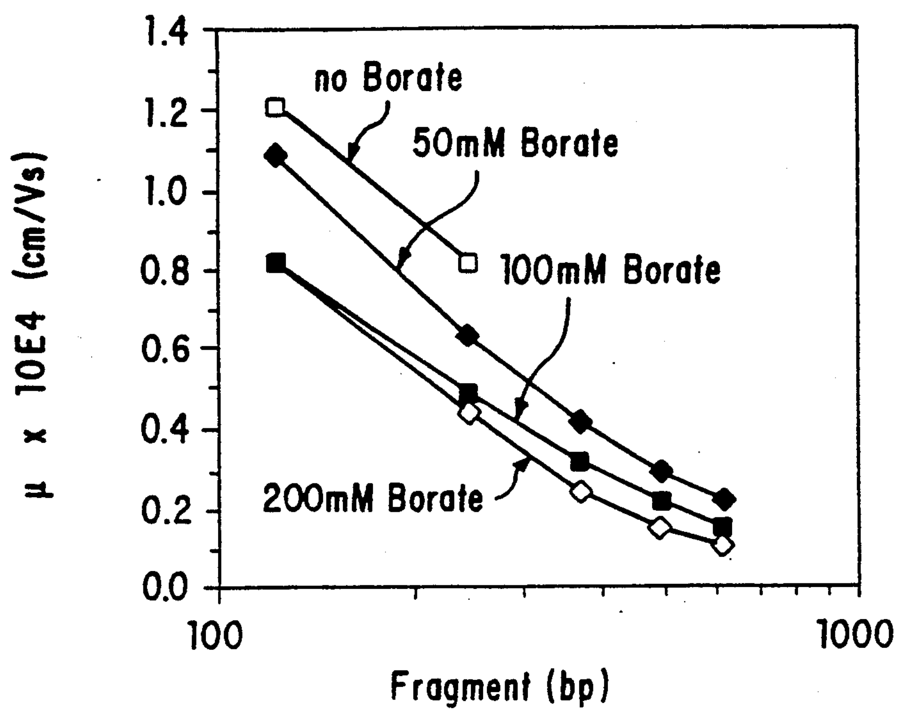
FIG. 3 shows the effects on sieving of different borate concentrations in glyceryl agarose gels of the invention.

Four glyceryl borate gels were made according to the process of Example 2 except that the aqueous solution contained 0, 50, 100, and 200 mM of $BH_3O_3$ respectively, together with 90 mM of Tris and 2 mM of EDTA and gels were cast in trays w/combs. In each gel, 300 ng of 123 base pair ladder from Life Technologies, Inc., catalog number 5613SA was loaded and the gels were electrophoresed at 4 V/cm. In FIG. 3, the results show the mobilities ($cm^2/Vs$) of the first five fragments in the ladder (123-615 bp).

EXAMPLE 19

Figure 4:
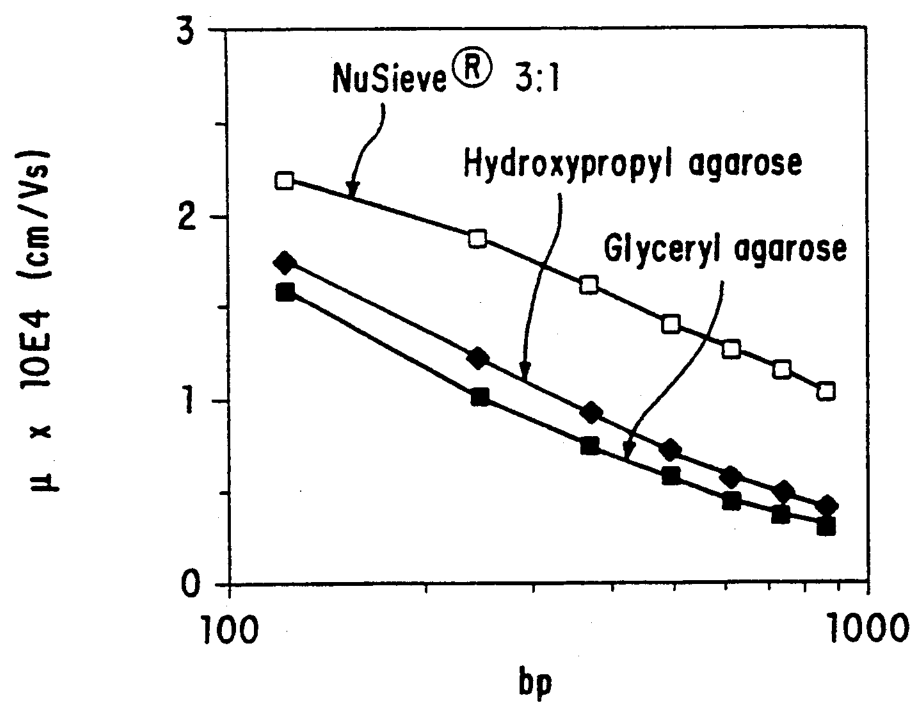
FIG. 4 gives a mobility comparison of three agarose gels including a glyceryl agarose gel of the invention.

Three gels were prepared according to the process of Example 2, except that 89 mM of $BH_3O_3$, 89 mM of Tris, and 2 mM of EDTA pH 8 were present, and wherein either 2% by weight concentrations of glyceryl agarose prepared by the process of Example 1, or hydroxypropyl agarose, or NuSieve® 3:1 were present in the gel. 500 ng of the 123 bp ladder was loaded into each gel. Electrophoresis was carried out for 2 hours and 55 minutes at 4 V/cm. The results show the mobilities of the first seven fragments (123-861 bp) in each of the gels, shown in FIG. 4.

EXAMPLE 20

Figure 5:
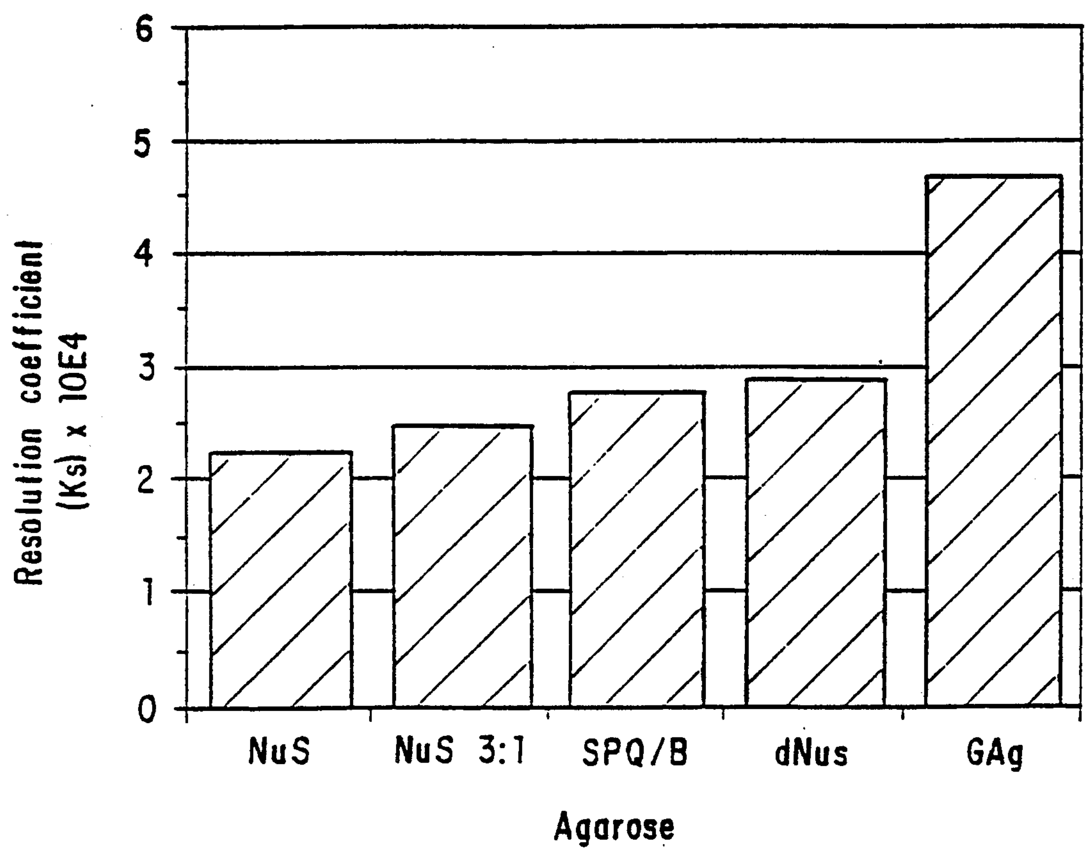
FIG. 5 gives a comparison of the resolution coefficients of five agarose gels combined with borate including a glyceryl agarose gel of the invention.

Studies on the resolution capabilities of various marketed and experimental gels compared to a glyceryl agarose gel of the invention were run with the nucleic acid 123 bp ladder and the first seven bands were compared (123-861 bp). The gels were made at various concentrations (1, 1.5, 2, 2.5 and 3% w/v) containing 89 mM $BH_3O_3$, 89 mM Tris, and 2 mM EDTA, at pH 8.0. They were electrophoresed at 4V/cm in a SeaKem® LE framing gel. The absolute mobilities ($cm^2/Vs$) of the fragments were determined in each of the agarose gels, and the resolution coefficients (Ks) were determined by plotting the square root of the retardation coefficients (Kr), as described by Ferguson (1964) and used by Serwer (1983) Ferguson, K. A., Metabolism 1964, 13, 985-1002 Serwer, P.; Allen, J. L.; Hayes, S. J., Electrophoresis 1983, 4, 232-236, against the log base 10 of the size of the fragments (in bp). The greater the value of the resolution coefficient, the greater the separation between fragments, and the better the resolution. The results are shown in FIG. 5.

EXAMPLE 21

Comparison of Inventive Gels 1(A) and 1(B) as to Break Force and Penetration

In order to ascertain the effect of using a more highly purified glyceryl agarose, two gels were prepared in accordance with Example 2, except beginning with gels according to Example 1(A) and 1(B). The results are as follows:

| Agarose/Borate | Break Force (g) | Penetration (mm) |
|---|---|---|
| Ex 1(A) | 249 | 17.1 |
| Ex 1(B) | 277 | 18.2 |

The small difference between the measured values indicates that the glyceryl agarose starting material did not make an appreciable difference in the results.

EXAMPLE 22

Comparison of Inventive Gels 1(A) and 1(B) as to Sieving Properties

In order to ascertain the effect of using a more highly purified glyceryl agarose, two inventive gels were prepared in accordance with Example 19, except beginning with glyceryl agarose according to Examples 1(A) and 1(B), and for a time of 3 hours 42 minutes. The mobilities in $(cm^2/volt\text{-}seconds) \times 10^4$ are:

| | Absolute Mobilities (Fragment Size) | | | | | | |
|---|---|---|---|---|---|---|---|
| | 123 | 246 | 369 | 492 | 615 | 738 | 861 |
| 1(A) | 1.58 | 1.10 | 0.822 | 0.625 | 0.494 | 0.328 | 0.328 |
| 1(B) | 1.49 | 1.00 | 0.723 | 0.542 | 0.428 | 0.394 | 0.263 |

It will be noted that the difference in mobility for any given fragment size is not appreciable, although gel 1(B) is slightly more sieving. The resolving power of the two glyceryl agarose components was essentially the same, as shown in FIG. 5.

I claim:

1. An aqueous gel composition characterized in that it comprises:

(A) at least one di-or tri-hydroxy alkyl ether moiety substituted gel-forming agarose present in a gel-forming effective amount;

(B) at least one borate compound other than a strongly reducing or strongly axoidizing compound present in a gel-handling-effective amount; and (C) water sufficient to form a gel.

2. The composition of claim 1 characterized in that the moiety is glyceryl.

3. The composition of claim 2 characterized in that said at least one borate compound is present in about 20 to 400 mM of aqueous gel composition.

4. The composition of claim 3 characterized in that said at least one borate compound is present in about 40 to 150 mM of aqueous gel composition.

5. The composition of claim 4 characterized in that said at least one borate compound is present in about 50 to 100 mM of aqueous gel composition.

6. The composition of claim 2 characterized in that it has a pH of about 3.0 to 12.0.

7. The composition of claim 6 characterized in that it has a pH of about 6.0 to 10.0.

8. The composition of claim 7 characterized in that it has a pH of about 7.5 to 9.5.

9. The composition of claim 8 characterized in that it has a pH of about 8.0 to 8.5.

10. The composition of claim 2 characterized in that said at least one glyceryl agarose is present in about 0.1 to 15% weight/volume.

11. The composition of claim 10 characterized in that said at least one glyceryl agarose is present in about 0.5 to 8% weight/volume.

12. The composition of claim 11 characterized in that said at least one glyceryl agarose is present in about 1 to 6% weight/volume.

13. The composition of claim 2 characterized in that the borate compound is at least one of $BH_3O_3$, alkali metal borate salts, alkaline earth metal borate salts, alkali metal organoboron compounds, and alkaline earth metal organoboron compounds.

14. The composition of claim 13 characterized in that the borate compound is $BH_3O_3$.

15. The composition of claim 2 characterized in that the glyceryl agarose contains about 0.08 to 1.3 glyceryl moieties per each agarose agarobiose unit.

16. The composition of claim 15 characterized in that the glyceryl agarose contains about 0.10 to 0.75 glyceryl moieties per each agarose agarobiose unit.

17. The composition of claim 2 characterized in that the glyceryl agarose is based on agarose derived from R. *Gelidium* or R. *Pterocladia.*

18. The composition of claim 2 characterized in that the pH of the composition is about 6.0 to about 10.0, and the at least one borate compound is $BH_3O_3$ present in about 50 to about 150 mM per liter of composition.

19. The composition of claim 2 characterized in that the pH is about 7.5 to 9.5, the at least one borate compound is $BH_3O_3$ present in about 80 to about 100 mM of composition, and the glyceryl agarose is present in about 1 to about 6% weight/volume.

20. A kit for the preparation of the composition of claim 2 upon admixture with water characterized in that it comprises measured amounts of:

(A) said at least one glyceryl agarose; and (B) said at least one borate compound.

21. The kit of claim 20 characterized in that the borate compound is $BH_3O_3$.

22. The kit of claim 21 characterized in that the glyceryl agarose has about 0.08 to 1.3 glyceryl moieties per each agarose agarobiose unit.

23. A method for gel electrophoresis characterized in that the gel used therein is an aqueous gel composition comprising:

(A) at least one di- or tri-hydroxy $C_{2-4}$ alkyl ether moiety substituted agarose present in a gel-forming-effective amount;

(B) at least one borate compound present in a gel-handling-effective amount; and (C) water sufficient to form a gel.

24. The method of claim 23 characterized in that the moiety is glyceryl.

25. The method of claim 24 characterized in that the pH of the gel composition is about 6.0 to 10.0, and the borate compound is $BH_3O_3$ present in about 50 to about 150 mM per liter of gel composition.

26. A method for imparting gel-handling properties to an aqueous glyceryl agarose gel characterized by admixing therewith a handling-effective amount of at least one borate prior to, during, or subsequent to, the formation of said gel.

27. The method of claim 26 characterized in that the pH of the gel composition is about 6.0 to 10.0, and the borate compound is $BH_3O_3$ present in about 50 to about 150 mM per liter of gel composition.

* * * * *